United States Patent [19]

Erdmann et al.

[11] Patent Number: 5,030,741

[45] Date of Patent: Jul. 9, 1991

[54] CYCLIC ORGANOMETALLIC COMPOUNDS

[75] Inventors: Dietrich Erdmann, Mühltal-Traisa; Ludwig Pohl, Darmstadt; Martin Hostalek, Darmstadt; Matthias Lokai, Darmstadt, all of Fed. Rep. of Germany

[73] Assignee: Merck Patent Gesellschaft mit Berschrankter Haftung, Darmstadt, Fed. Rep. of Germany

[21] Appl. No.: 353,740

[22] Filed: May 18, 1989

[30] Foreign Application Priority Data

May 19, 1988 [DE] Fed. Rep. of Germany ....... 3817090

[51] Int. Cl.$^5$ ............................. C07F 5/00; C07F 5/06

[52] U.S. Cl. ............................................ 556/1; 556/2; 556/4; 556/5; 556/14; 556/27; 556/28; 556/30; 556/170; 556/174; 556/186

[58] Field of Search ........................ 556/1, 2, 4, 5, 13, 556/30, 14, 27, 28, 30, 170, 174, 186

[56] References Cited

U.S. PATENT DOCUMENTS 4,621,147 11/1986 Beachley, Jr. ........................ 556/1

*Primary Examiner*—Arthur C. Prescott
*Attorney, Agent, or Firm*—Millen, White & Zelano

[57] ABSTRACT

The invention relates to cyclic organometallic compounds which are intramolecularly stabilized and also to their use to produce thin films and epitaxial layers by gas-phase deposition.

18 Claims, No Drawings

CYCLIC ORGANOMETALLIC COMPOUNDS

BACKGROUND OF THE INVENTION

The invention relates to cyclic organometallic compounds which contain aluminum, gallium or indium as metals and also to the use of said compounds for producing thin films or epitaxial layers by gas-phase deposition.

The deposition of such layers composed either of pure elements of group III or of combinations with other elements, such as, for example, gallium arsenide, indium phosphide or gallium phosphide, may be used to produce electronic and optoelectronic switching elements, compound semiconductors and lasers. Such layers are deposited from the gas phase.

The properties of these films depend on the deposition conditions and the chemical composition of the film deposited.

All the known methods, such as the Metal-Organic Chemical Vapor Deposition (MOCVD) Method, the Photo-Metal-Organic Vapor Phase (Photo-MOVP) Method in which the substances are decomposed by UV irradiation, the Laser Chemical Vapor Deposition (Laser CVD) Method or the Metal-Organic Magnetron Sputtering (MOMS) Method are suitable for the deposition from the gas phase. The advantages over other methods are a controllable layer growth, a precise doping control and also easy handling and convenience of production owing to the normal-pressure or low-pressure conditions.

In the MOCVD Method, use is made of organometallic compounds which decompose at a temperature below 1100° C. to deposit the metal. Typical apparatuses which are at present used for MOCVD comprise a "bubbler" with an inlet for the organometallic component, a reaction chamber which contains the substrate to be coated, and also a source for a carrier gas which should be inert towards the organometallic component. The "bubbler" is kept at a constant, relatively low temperature which is preferably above the melting point of the organometallic compound but far below the decomposition temperature. The reaction or decomposition chamber is preferably at a very much higher temperature which is below 1100° C., at which temperature the organometallic compound decomposes completely and the metal is deposited. The carrier gas converts the organometallic compound to the vapor state and the latter is then channelled along with the carrier gas into the decomposition chamber. The mass flow of the vapor can be controlled satisfactorily, and consequently, controlled growth of the thin layers is also possible.

Hitherto, metal alkyls such as, for example, trimethylgallium, trimethylaluminum or trimethylindium have mainly been used for the gas-phase deposition. These compounds are, however, extremely sensitive to air, spontaneously ignitable and in some cases are decomposable even at room temperature. Elaborate safety measures are therefore necessary for producing, transporting, storing and using these compounds. A few, somewhat more stable adducts of the metal alkyls with Lewis bases such as, for example, trimethylamine and triphenylphosphine are also known (described, for example, in GB Patent Specification 2,123,422, EP-A-108,469 or EP-A-176,537), but these have only limited suitability for gas-phase deposition owing to the low vapor pressure.

Furthermore, similar compounds are described in German Offenlegungsschrift 3,631,469 but these do not have a cyclic structure with the metal in the cycle.

SUMMARY OF THE INVENTION

An object of the present invention is therefor to find metal alkyl compounds which can be handled simply and are stable at room temperature and which can be decomposed from the gas phase, that is to say are suitable for the various methods of gas-phase deposition.

Upon further study of the specification and appended claims, further objects and advantages of this invention will become apparent to those skilled in the art.

Surprisingly, it has now been found that certain cyclic compounds of aluminum, gallium and indium are outstanding for a high stability towards air and oxygen, are therefore simple to handle and are eminently suitable for gas-phase deposition.

The invention therefore relates to cyclic organometallic compounds of the formula I

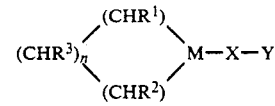

wherein
M is aluminum, gallium or indium,
n is 1, 2, 3, 4, 5 or 6,
X is $-(CHR^4)_m-$ where m = 1, 2, 3, 4 or 5,
o—$(CH_2)_p$—$C_6H_4$—$(CH_2)_q$—,
o—$(CH_2)_p$—$C_6H_{10}$—$(CH_2)_q$—,
o—$(CH_2)_p$—$C_6H_8$—$(CH_2)_q$—,
o—$(CH_2)_p$—$C_6H_6$—$(CH_2)_q$—,
o—$(CH_2)_p$—$C_5H_8$—$(CH_2)_q$—,
o—$(CH_2)_p$—$C_5H_6$—$(CH_2)_q$—,
o—$(CH_2)_p$—$C_5H_4$—$(CH_2)_q$—,
o—$(CH_2)_p$—$C_4H_6$—$(CH_2)_q$—,
if $Y = -F$, $-CF_3$, $-C_2F_5$, $-C_3F_7$, or $-C_4F_9$, also a single bond,
p and q are, in each case independently of each other, 0, 1, 2 or 3,
$R^1$, $R^2$, $R^3$ and $R^4$ are, in each case independently of each other, H or an alkyl group containing 1-4 carbon atoms,
Y is $-NR^5R^6$, $-PR^5R^6$, $-AsR^5R^6$, $-SbR^5R^6$, $-F$, $-CF_3$, $-C_2F_5$, $-C_3F_7$ or $-C_4F_9$, and
$R^5$ and $R^6$ are, in each case independently of each other, an alkyl group containing 1-8 carbon atoms, it being possible for the alkyl group to be partially or completely fluorinated, a cycloalkyl group, alkenyl group or cycloalkenyl group containing, in each case, 3-8 carbon atoms, or a phenyl group.

The invention furthermore relates to the use of compounds of formula I for gas-phase deposition and also to a process for producing thin films or epitaxial layers by gas-phase deposition of the metal from organometallic compounds in which the compounds of formula I are used as organometallic substances.

The compounds of the formula I have a cyclic structure and are intramolecularly stabilized by electron transfer from the nitrogen, phosphorus, arsenic, antimony or fluorine atom to the electron-deficient III B element. Compared with the metal alkyls hitherto used, they therefore have high stability towards air and oxygen. They are no longer spontaneously ignitable and are consequently simple to handle. In the gas phase, however, the compounds according to the invention can easily be decomposed to deposit the metal.

In formula I, M is aluminum (Al), gallium (Ga) or indium (In), preferably Ga or In.

The parameter n is 1, 2, 3, 4, 5 or 6, preferably 2, 3 or 4. X is preferably —(CHR$^4$)$_m$, where m=1, 2, 3, 4 or 5, preferably m is 2, 3 or 4.

R$^1$, R$^2$, R$^3$ and R$^4$ are, independently of each other, a hydrogen atom or a methyl, ethyl, propyl, isopropyl, butyl, sec-butyl or tert-butyl group. Preferably, R$^1$, R$^2$, R$^3$ and R$^4$ are each a hydrogen atom. If n or m>1, at most a R$^3$ or a R$^4$ radical is preferably an alkyl group and the other R$^3$ or R$^4$ radicals respectively are then hydrogen. Therefore, if a plurality of R$^3$ or R$^4$ radicals is present, they may be identical or different.

Preferred are also compounds of the formula I in which X is o—(CH$_2$)$_p$—C$_6$H$_4$—(CH$_2$)$_q$—,  o—(CH$_2$)$_p$—C$_6$H$_{10}$—(CH$_2$)$_q$—, o—(CH$_2$)$_p$—C$_6$H$_8$—(CH$_2$)$_q$—,  o—(CH$_2$)$_p$—C$_6$H$_6$—(CH$_2$)$_q$—, o—(CH$_2$)$_p$—C$_5$H$_8$—(CH$_2$)$_q$—,  o—(CH$_2$)$_p$—C$_5$H$_6$—(CH$_2$)$_q$—, o—(CH$_2$)$_p$—C$_5$H$_4$—(CH$_2$)$_q$—,  o—(CH$_2$)$_p$—C$_4$H$_6$—(CH$_2$)$_q$—.

p and q are, in each case independently of each other, 0, 1, 2 or 3, preferably 1 or 2. At the same time those compounds are preferred in which one of the groups p and q is 0 and the other is 1 or 2.

The following formulae (1) to (16) are preferred representatives of the grouping —X—Y:

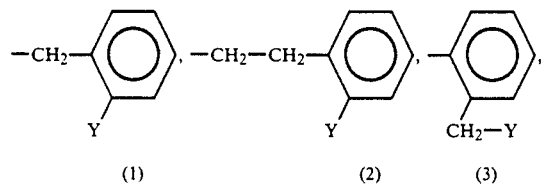
(1) (2) (3)

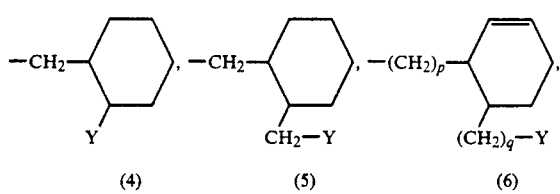
(4) (5) (6)

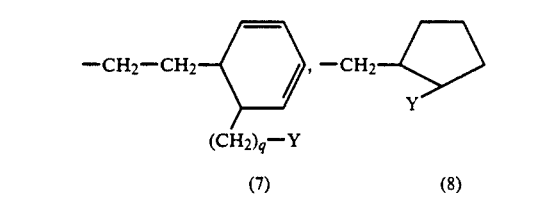
(7) (8)

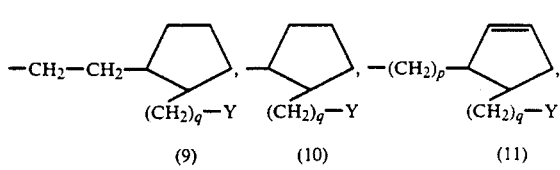
(9) (10) (11)

-continued

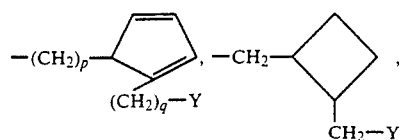
(12) (13)

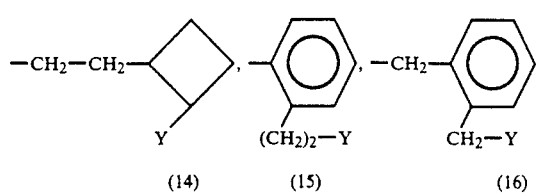
(14) (15) (16)

X may be a single bond, particularly in those cases where Y is, —F, —CF$_3$, —C$_2$F$_5$, —C$_3$F$_7$ or —C$_4$F$_9$.

Y in formula I is preferably —NR$^5$R$^6$, —PR$^5$R$^6$ or —AsR$^5$R$^6$, and furthermore —SbR$^5$R$^6$. Preferred, in particular, is —NR$^5$R$^6$.

Compounds of formula I are furthermore preferred in which Y is —F, —CF$_3$ or —C$_2$F$_5$.

The R$^5$ and R$^6$ radicals in formula I may in each case be a straight-chain or branched alkyl group containing 1-8 carbon atoms, preferably containing 1-4 carbon atoms. They are preferably straight-chain and are accordingly preferably methyl, ethyl, propyl, butyl, and furthermore pentyl, hexyl, heptyl, octyl, iso-propyl, sec-butyl, tert-butyl, 2-methylpentyl, 3-methylpentyl or 2-octyl. The alkyl radicals may be partially or even completely fluorinated and may be, for example, monofluoromethyl, trifluoromethyl, difluoroethyl, trifluoroethyl, pentafluoroethyl or trifluoropropyl.

If R$^5$ or R$^6$ is a cycloalkyl group or a cycloalkenyl group containing 3-8 carbon atoms, it is preferably cyclopropyl, cyclobutyl, cyclopentyl, cyclopentenyl, cyclohexyl, cyclohexenyl, cyclohexadienyl, cycloheptyl, cycloheptenyl, cycloheptadienyl, cyclooctyl, cyclooctenyl, cyclooctadienyl, cyclooctatrienyl or cyclooctatetraenyl.

Preferably, R$^5$ and/or R$^6$ are also alkenyl groups containing 3-8 carbon atoms, preferably containing 3-5 carbon atoms. They are accordingly preferably propenyl, butenyl, pentenyl, and furthermore, hexenyl, heptenyl or octenyl.

Furthermore, those compounds of formula I are preferred in which R$^5$ and/or R$^6$ are a phenyl group. Said phenyl group may also be substituted. Since these substituents do not have any substantial effect on the intended application, all those substituents are permissible which do not have any disturbing effect on the decomposition reaction.

The following compounds are a smaller group of particularly preferred compounds of the formula I:

1-galla-1-(3-dimethylaminopropyl)cyclopentane
1-galla-1-(2-dimethylaminoethyl)cyclopentane
1-inda-1-(3-diethylaminopropyl)cyclopentane
1-alumina-1-(3-dimethylaminopropyl)cyclopentane
1-galla-1-(3-dimethylaminopropyl)cyclobutane
1-inda-1-(2-diethylaminoethyl)cyclobutane
1-alumina-1-(4-dimethylaminobutyl)cyclobutane
1-galla-1-(o-dimethylaminobenzyl)cyclohexane
1-galla-1-(o-dimethylaminobenzyl)cyclobutane
1-alumina-1-(o-diethylaminobenzyl)cyclopentane
1-alumina-1-(o-diethylaminobenzyl)cyclohexane 1-inda-1-(o-diisopropylaminobenzyl)cyclobutane
1-inda-1-(o-dimethylaminobenzyl)cyclopentane
1-inda-1-(o-dimethylaminobenzyl)cyclohexane
1-galla-1-(o-dimethylaminobenzyl)cyclopentane
1-galla-1-(o-diethylaminobenzyl)cyclohexane
1-galla-1-(o-dipropylaminobenzyl)cycloheptane
1-inda-1-(o-dibutyl-aninobenzyl)cyclopentane
1-inda-1-(o-diethylaminobenzyl)cyclohexane
1-inda-1-(o-dimethylaminobenzyl)cyclooctane
1-alumina-1-(o-di-isopropylaminobenzyl)cyclohexane
1-alumina-1-(2-o-dimethylaminophenylethyl)cyclopentane
1-alumina-1-(2-o-diethylaminophenylethyl)cyclobutane
  1-galla-1-($X$-$PR^5R^6$)cyclopentane
  1-galla-1-($X$-$PR^5R^6$)cyclobutane
  1-galla-1-($X$-$PR^5R^6$)cyclohexane
  1-alumina-1-($X$-$PR^5R^6$)cyclopentane
  1-alumina-1-($X$-$PR^5R^6$)cyclohexane
  1-inda-1-($X$-$PR^5R^6$)cyclopentane
  1-inda-1-($X$-$AsR^5R^6$)cyclohexane
  1-inda-1-($X$-$AsR^5R^6$)cyclopentane
  1-inda-1-($X$-$SbR^5R^6$)cyclopentane
  1-alumina-1-($X$-$AsR^5R^6$)cycloheptane
  1-galla-1-($X$-$SbR^5R^6$)cyclooctane
  1-galla-1-($X$-$CF_3$)cyclobutane
  1-galla-1-($X$-$F$)cyclopentane
  1-galla-1-trifluoromethylcyclopentane
  1-galla-1-trifluoromethylcyclohexane
  1-inda-1-trifluoromethylcyclohexane
  1-inda--fluorocyclopentane
  1-alumina-1-pentafluoroethylcyclohexane
  1-galla-1-pentafluoroethylcyclopentane
  1-galla-1-fluorocycloheptane
  1-alumina-1-fluorocyclohexane
  1-galla-1-heptafluoropropylcyclopentane
  1-galla-1-($X$-$C_2F_5$)cyclopentane
  1-inda-1-($X$-$C_3F_7$)cyclohexane
  1-galla-1-($X$-$C_4F_9$)cyclopentane.

The compounds of the formula I are eminently suitable for MOCVD epitaxy or the MCCVD method, since they decompose at elevated temperatures to liberate the corresponding metal. They are also suitable for other methods of gas-phase deposition such as photo-MOVP, laser CVD or MOMS.

The compounds of the formula I are prepared by methods known per se as they are described in the literature (for example, G Bähr and P. Burba, Methoden der Organischen Chemie, Bd. XIII/4, Georg Thieme Verlag, Stuttgart (1970)), and in particular, under reaction conditions which are known and suitable for said reactions. At the same time, use may also be made of variants known per se but not mentioned here.

Thus, compounds of the formula I can be prepared, for example, by reacting metal alkyl chlorides with an alkali-metal organyl of the corresponding Lewis base or a Grignard compound in an inert solvent.

The reactions are preferably carried out in inert solvents. At the same time, all those solvents are suitable which do not interfere with the reaction and do not enter into the reaction process. The reaction temperatures essentially correspond to those which are known from the literature for the preparation of similar compounds.

In the process according to the invention for producing thin films or epitaxial layers on any desired substrates, use is made of the intramolecularly stabilized organometallic compounds of the formula I as starting compounds in the gas-phase deposition processes of organometallic compounds, known per se.

To produce compound semiconductors, one or more compounds of arsenic, antimony or phosphorus which are gaseous under the reaction conditions used, for example $AsH_3$, $As(CH_3)_3$, $PH_3$ or $SbH_3$, are added during the deposition process in the decomposition chamber.

A further variant of the process according to the invention is to add dopants during the deposition process in addition to the organometallic compounds of the formula I according to the invention. In this connection, volatile organometallic compounds cf iron, magnesium, zinc or chromium are used as dopants. Preferred compounds for this purpose are considered to be, for example, $Zn(CH_3)_2$, $Mg(CH_3)_2$ or $Fe(C_5H_5)_2$.

The layers produced by the process according to the invention can be used to produce electronic or optoelectronic circuit components, compound semiconductors or lasers.

Since only approx. 1–10% of the free metal alkyls used can be deposited on the substrate as an epitaxial layer in the epitaxial plants at present in use for thermodynamic reasons, the destruction of excess metal alkyls, which cannot be recovered owing to their extreme sensitivity, presents a substantial problem.

The compounds of the formula I according to the invention, on the other hand, open up new possibilities for the safe destruction or for the recovery of the valuable III B compounds owing to their high stability.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

The entire texts of all applications, patents and publications cited above and of corresponding application German P 38 17 090.6, filed May 19, 1988, are hereby incorporated by reference.

EXAMPLES

The following examples are intended to explain the invention in more detail. Temperatures are given in degrees Celsius or Kelvin. m.p. is the melting point and b.p. is the boiling point.

EXAMPLE 1

0.64 mol of magnesium chips activated with iodine are placed in 200 ml of diethyl ether. After adding 0.16 mol of 1,4-dichlorobutane, the mixture is heated for 3 hours under reflux.

0.15 mol of 3-dimethylaminoprcpylgallium dichloride in 250 ml of diethyl ether is added to this Grignard solution at 0°. The reaction mixture is stirred for a further hour at room temperature, the volatile constituents are distilled off at a bath temperature of up to 200° and a pressure of $10^{-2}$ mbar and a fractional distillation of the distillate gives 1-galla-1-(3-dimethylaminopropyl)cyclopentane methylaminopropyl)cyclopentane as a clear liquid stable in air.

Mass spectrum: m/e ($I_{rel.}$)=225 (35; $M^+$); 182 (52; $M^+$, $-C_3H_7$); 155 (40; $M^+$, $-C_5H_{10}$); 86 (53; $(CH_3)_2$-$N$-$(CH_2)_3^+$); 58 (100; $(CH_3)_2NCH_2^+$).

The following are prepared analogously:
  1-galla-1-(2-dimethylaminoethyl)cyclopentane 1-galla-1-(2-diethylaminoethyl)cyclopentane
1-galla-1-(2-dipropylaminoethyl)cyclopentane
1-galla-1-(2-di-isopropylaminoethyl)cyclopentane
1-galla-1-((2-dibutylaminoethyl)cyclopentane
1-galla-1-(3-diethylaminopropyl)cyclopentane
1-galla-1-(3-dipropylaminopropyl)cyclopentane
1-galla-1-(3-di-isopropylaminopropyl)cyclopentane
1-galla-1-(3-dibutylaminopropyl)cyclopentane
1-galla-1-(4-dimethylaminobutyl)cyclopentane
1-galla-1-(4-diethylaminobutyl)cyclopentane
1-qalla-1-(4-dipropylaminobutyl)cyclopentane
1-galla-1-(4-di-isopropylaminobutyl)cyclopentane
1-galla-1-(4-dibutylaminobutyl)cyclopentane
1-alumina-1-(3-dipropylaminopropyl)cyclopentane
1-alumina-1-(3-di-isopropylaminopropyl)cyclopentane
1-alumina-1-(3-dipropylaminopropyl)cyclopentane
1-alumina-1-(3-di-isopropylaminopropyl)cyclopentane
1-alumina-1-(3-dibutylaminopropyl)cyclopentane
1-alumina-1-(2-dimethylaminoethyl)cyclopentane
1-alumina-1-(2-diethylaminoethyl)cyclopentane
1-alumina-1-(2-dipropylaminoethyl)cyclopentane
1-alumina-1-(2-di-isopropylaminoethyl)cyclopentane
1-alumina-1-(2-dibutylaminoethyl)cyclopentane
1-alumina-1-(4-dimethylaminobutyl)cyclopentane
1-alumina-1-(4-diethylaminobutyl)cyclopentane
1-alumina-1-(4-dipropylaminobutyl)cyclopentane
1-alumina-1-(4-di-isopropylaminobutyl)cyclopentane
1-alumina-1-(4-dibutylaminobutyl)cyclopentane
1-inda-1-(3-dimethylaminopropyl)cyclopentane
1-inda-1-(3-diethylaminopropyl)cyclopentane
1-inda-1-(3-dipropylaminopropyl)cyclopentane
1-inda-1-(3-di-isopropylaminopropyl)cyclopentane
1-inda-1-(3-dibutylaminopropyl)cyclopentane
1-inda-1-(2-dimethylaminoethyl)cyclopentane
1-inda-1-(2-diethylaminoethyl)cyclopentane
1-inda-1-(2-dipropylaminoethyl)cyclopentane
1-inda-1-(2-di-isopropylaminoethyl)cyclopentane
1-inda-1-(2-dibutylaminoethyl)cyclopentane
1-inda-1-(4-dimethylaminobutyl)cyclopentane
1-inda-1-(4-diethylaminobutyl)cyclopentane
1-inda-1-(4-dipropylaminobutyl)cyclopentane
1-inda-1-(4-di-isopropylaminobutyl)cyclopentane
1-inda-1-(4-dibutylaminobutyl)cyclopentane.

EXAMPLE 2

0.25 mol of magnesium chips activated with iodine are place in 100 ml of diethyl ether. After adding 0.66 mol of 1,5-dichloropentane at room temperature, the mixture is heated under reflux for 3 hours.

The Grignard solution decanted from the magnesium and 0.06 mol of 3-dimethylaminopropylgallium dichloride dissolved in 150 ml of ether are synchronously brought together while stirring vigorously for the purpose of reaction.

The reaction mixture is then stirred at room temperature. The volatile constituents are distilled off at a bath temperature of up to 180° and a pressure of $10^{-2}$ mbar and fractionally distilled yet again. This gives 1-galla-1-(3-dimethylaminopropyl)cyclchexane as a water-clear liquid which is stable in air.

Mass spectrum: m/e ($I_{rel.}$) 211 (17; M+); 155 ( 40; M+, -$C_4H_8$); 86 (66; $(CH_3)_2$N-$(CH_2)_3^+$); 58 (100; $(CH_3)_2$N-$CH_2^+$).

The following are prepared analogously:
1-galla-1-(3-diethylaminopropyl)cyclohexane
1-galla-1-(3-dipropylaminopropyl)cyclohexane
1-galla-1-(3-di-isopropylaminopropyl)cyclohexane
1-galla-1-(3-dibutylaminopropyl)cyclohexane
1-galla-1-(2-dimethylaminoethyl)cyclohexane
1-galla-1-(2-diethylaminoethyl)cyclohexane
1-galla-1-(2-dipropylaminoethyl)cyclohexane
1-galla-1-(2-di-isopropylaminoethyl)cyclohexane
1-galla-1-(2-dibutylaminoethyl)cyclohexane
1-galla-1-(4-dimethylaminobutyl)cyclohexane
1-galla-1-(4-diethylaminobutyl)cyclohexane
1-galla-1-(4-dipropylaminobutyl)cyclohexane
1-galla-1-(4-di-isopropylaminobutyl)cyclohexane
1-galla-1-(4-dibutylaminobutyl)cyclohexane
1-alumina-1-(3-dimethylaminopropyl)cyclohexane
1-alumina-1-(3-diethylaminopropyl)cyclohexane
1-alumina-1-(3-dipropylaminopropyl)cyclohexane
1-alumina-1-(3-di-isopropylaminopropyl)cyclohexane
1-alumina-1-(3-di-isopropylaminopropyl)cyclohexane
1-alumina-1-(3-dibutylaminopropyl)cyclohexane
1-alumina-1-(2-dimethylaminoethyl)cyclohexane
1-alumina-1-(2-diethylaminoethyl)cyclohexane
1-alumina-1-(2-dipropylaminoethyl)cyclohexane
1-alumina-1-(2-di-isopropylaminoethyl)cyclohexane
1-alumina-1-(2-dibutylaminoethylacyclohexane
1-alumina-1-(4-dimethylaminobutyl)cyclohexane
1-alumina-1-(4-diethylaminobutyl)cyclohexane
1-alumina-1-(4-dipropylaminobutyl)cyclohexane
1-alumina-1-(4-di-isopropylaminobutyl)cyclohexane
1-alumina-1-(4-dibutylaminobutyl)cyclohexane
1-inda-1-(3-dimethylaminopropyl)cyclohexane
1-inda-1-(3-diethylaminopropyl)cyclohexane
1-inda-1-(3-dipropylaminopropyl)cyclohexane
1-inda-1-(3-di-isopropylaminopropyl)cyclohexane
1-inda-1-(3-dibutylaminopropyl)cyclohexane
1-inda-1-(2-dimethylaminoethyl)cyclohexane
1-inda-1-(2-diethylaminoethyl)cyclohexane
1-inda-1-(2-dipropylaminoethyl)cyclohexane
1-inda-1-(2-di-isopropylaminoethyl)cyclohexane
1-inda-1-(2-dibutylaminoethyl)cyclohexane
1-inda-1-(4-dimethylaminobutyl)cyclohexane
1-inda-1-(4-diethylaminobutyl)cyclohexane
1-inda-1-(4-dipropylaminobutyl)cyclohexane
1-inda-1-(4-di-isopropylaminobutyl)cyclohexane
1-inda-1-(4-dibutylaminobutyl)cyclohexane.

Example of the production of thin films

Example A

The "bubbler" is filled with 1-galla-1-(3-dimethylaminopropyl)cyclohexane (prepared according to Example 2) which is then connected to the gas inlet for the inert gas and the decomposition chamber. Depending on the partial pressure of the reagent in the reactor, decomposition takes place at temperatures of approx. 700° with deposition of gallium.

Example B

Epitaxial growth is carried out with (3-dimethylaminopropyl)-1-gallacyclohexane and $AsH_2$ in a low-pressure MOCVD plant (1000 - 2000 Pa). The growth temperatures were between 850 K and 1050 K. The electron mobility in the epitaxially GaAs layer at 77 K was $\mu_{77}=51000$ cm$^2$/Vs with a charge carrier concentration of $n_{77}=8\times10^{14}$ cm$^{-3}$. Incorporation of nitrogen was not observed.

Example C

Epitaxial growth was carried out with (3-dimethylaminopropyl)-1-aluminacyclohexane, Et$_3$Ga and AsH$_3$ in a low-pressure MOCVD plant (1000–2000 Pa). The growth temperatures were between 850 K and 1050 K. The electron mobility in the epitaxially grown AlGaAs layer at 77 K was $\mu_{77}$=6900 cm$^2$/Vs. Incorporation of nitrogen was not observed.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A cyclic organometallic compound of the formula I

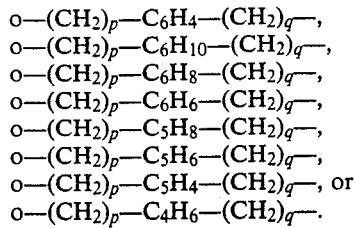

wherein
M is aluminum, gallium or indium;
n is 1, 2, 3, 4, 5 or 6;
X is —(CHR$^4$)$_m$— where m=1, 2, 3, 4 or 5,
o—(CH$_2$)$_p$—C$_6$H$_4$—(CH$_2$)$_q$—,
o—(CH$_2$)$_p$—C$_6$H$_{10}$—(CH$_2$)$_q$—,
o—(CH$_2$)$_p$—C$_6$H$_8$—(CH$_2$)$_q$—,
o—(CH$_2$)$_p$—C$_6$H$_6$—(CH$_2$)$_q$—,
o—(CH$_2$)$_p$—C$_5$H$_8$—(CH$_2$)$_q$—,
o—(CH$_2$)$_p$—C$_5$H$_6$—(CH$_2$)$_q$—,
o—(CH$_2$)$_p$—C$_5$H$_4$—(CH$_2$)$_q$—, or
o—(CH$_2$)$_p$—C$_4$H$_6$—(CH$_2$)$_q$—;

X can also be a single bond if Y is —F, —CF$_3$, —C$_2$F$_5$, —C$_3$F$_7$ or —C$_4$F$_9$;

p and q are, in each case independently of each other, 0, 1, 2 or 3;

R$^1$, R$^2$, R$^3$ and R$^4$ are, in each case independently of each other, H or an alkyl group containing 1–4 carbon atoms;

Y is —NR$^5$R$^6$, —PR$^5$R$^6$, —AsR$^5$R$^6$, —SbR$^5$R$^6$, —F, —CF$_3$, —C$_2$F$_5$, —C$_3$F$_7$ or —C$_4$F$_9$; and R$^5$ and R$^6$ are, in each case independently of each other, an alkyl group containing 1–8 carbon atoms, an alkyl group having 1–8 carbon atoms which is partially or completely fluorinated, a cycloalkyl group, alkenyl group or cycloalkenyl group having in each case 3–8 carbon atoms, or a phenyl group.

2. A compound according to claim 1, wherein M is In or Ga.

3. A compound according to claim 1, wherein m is 2, 3 or 4.

4. A compound according to claim 1, wherein X is —(CHR$^4$)$_m$—.

5. A compound according to claim 4, wherein m is 2, 3 or 4.

6. A compound according to claim 1, wherein either n or m is greater than 1 and one of the radicals R$^3$ and R$^4$ is an alkyl group and the other is H.

7. A compound according to claim 1, wherein X is
o—(CH$_2$)$_p$—C$_6$H$_4$—(CH$_2$)$_q$—,
o—(CH$_2$)$_p$—C$_6$H$_{10}$—(CH$_2$)$_q$—,
o—(CH$_2$)$_p$—C$_6$H$_8$—(CH$_2$)$_q$—,
o—(CH$_2$)$_p$—C$_6$H$_6$—(CH$_2$)$_q$—,
o—(CH$_2$)$_p$—C$_5$H$_8$—(CH$_2$)$_q$—,
o—(CH$_2$)$_p$—C$_5$H$_6$—(CH$_2$)$_q$—,
o—(CH$_2$)$_p$—C$_5$H$_4$—(CH$_2$)$_q$—, or
o—(CH$_2$)$_p$—C$_4$H$_6$—(CH$_2$)$_q$—.

8. A compound according to claim 1, wherein p and q are independently of each other, 1 or 2.

9. A compound according to claim 1, wherein one or the radical p and q is 0 and the other is 1 or 2.

10. A compound according to claim 1, wherein the group —X—Y is

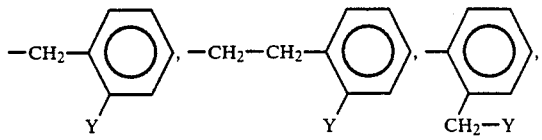

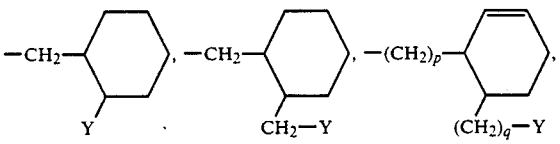

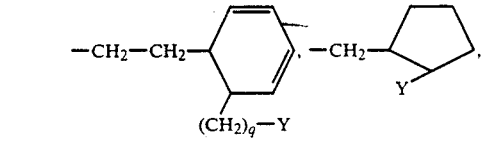

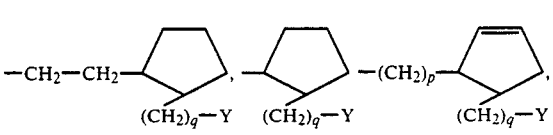

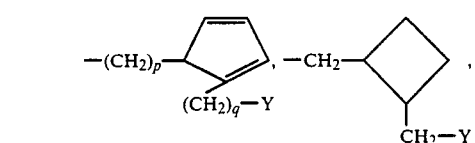

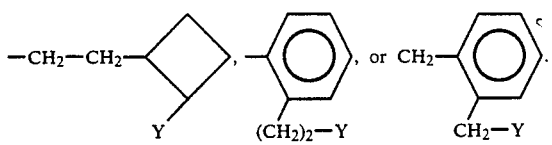

11. A compound according to claim 1, wherein X is a single bond and Y is —F, —CF$_3$, —C$_2$F$_5$, —C$_3$F$_7$ or —C$_4$F$_9$.

12. A compound according to claim 1, wherein Y is —NR$^5$R$^6$.

13. A compound according to claim 1, wherein Y is —F, —CF$_3$ or —C$_2$F$_5$.

14. A compound according to claim 1, wherein R$^5$ and R$^6$ are each independently straight chain or branched alkyl groups having 1–4 carbon atoms or partially or completely fluorinated straight chain or branched alkyl groups having 1–4 carbon atoms.

15. A compound according to claim 1, wherein either or both R$^5$ and R$^6$ are alkenyl groups having 3–5 carbon atoms.

16. 1-galla-1-(3-dimethylaminopropyl)cyclopentane, 1-galla-1-(2-dimethylaminoethyl)cyclopentane, 1-inda-1-(3-diethylaminopropyl)cyclopentane, 1-alumina-1-(3-dimethylaminopropyl)cyclopentane, 1-galla-1-(3-dimethylaminopropyl)cyclobutane, 1-inda-1-(2-diethylaminoethyl)cyclobutane, 1-alumina-1-(4-dimethylaminobutyl)cyclobutane, 1-galla-1-(o-dimethylaminobenzyl)cyclobutane, 1-alumina-1-(o-diethylaminobenzyl)cyclopentane, 1-alumina-1-(o-diethylaminobenzyl)cyclohexane, 1-inda-1-(o-diisopropylaminobenzyl)cyclobutane, 1-inda-1-(o-dimethylaminobenzyl)cyclopentane, 1-inda-1-(o-dimethylaminobenzyl)cyclohexane, 1-galla-1-(o-dimethylaminobenzyl)cyclopentane, 1-galla-1-(o-diethylaminobenzyl)cyclohexane, 1-galla-1-(o-dipropylaminobenzyl)cycloheptane, 1-inda-1-(o-dibutylaminobenzyl)cyclopentane, 1-inda-1-(o-diethylaminobenzyl)cyclohexane, 1-inda-1-(o-dimethylaminobenzyl)cyclooctane, 1-alumina-1-(o-di-isopropylaminobenzyl)cyclohexane, 1-alumina-1-(2-o-dimethylaminophenylethyl)cyclopentane, 1-alumina-1-(2-o-diethylaminophenylethyl)cyclobutane, 1-galla-1-trifluoromethylcyclopentane, 1-galla-1-trifluoromethylcyclohexane, 1-inda-1-trifluoromethylcyclohexane, 1-inda-1-fluorocyclopentane, 1-alumina-1-pentafluoroethylcyclohexane, 1-galla-1-pentafluoroethylcyclopentane, 1-galla-1-fluorocycloheptane, 1-alumina-1-fluorocyclohexane or 1-galla-1-heptafluoropropylcyclopentane, each a compound of claim 1.

17. A compound according to claim 1, wherein said compound is of the formula:

1-galla-1-(X-PR$^5$R$^6$)cyclopentane,
1-galla-1-(X-PR$^5$R$^6$)cyclobutane,
1-galla-1-(X-PR$^5$P$^6$)cyclohexane,
1-alumina-1-(X-PR$^5$P$^6$)cyclopentane,
1-alumina-1l-(X-PR$^5$R$^6$)cyclohexane,
1-inda-1-(X-PR$^5$R$^6$)cyclopentane,
1-inda-1-(X-AsR$^5$R$^6$)cyclohexane,
1-inda-1-(X-AsR$^5$R$^6$)cyclopentane,
1-inda-1-(X-SbR$^5$R$^6$)cyclopentane,
1-alumina-1-(X-AsR$^5$R$^6$)cycloheptane,
1-galla-1-(X-SbR$^5$R$^6$)cyclooctane,
1-galla-1-(X-CF$_3$)cyclobutane,
1-galla-1-(X-F)cyclopentane,
1-galla-1-(X-C$_2$F$_5$)cyclopentane,
1-inda-1-(X-C$_3$F$_7$)cyclohexane or
1-galla-1(X-C$_4$F$_9$)cyclopentane.

18. A compound according to claim 1, wherein said compound is 1-galla-1-(3-dimethylaminopropyl)-cyclohexane or 1-galla-1-(3-dimethylaminopropyl)-cyclopentane.

* * * * *